(12) United States Patent
Armstrong et al.

(10) Patent No.: US 6,340,573 B1
(45) Date of Patent: Jan. 22, 2002

(54) CHROMOGENIC SUBSTRATES FOR DETECTING BACTERIAL HYDROLASES

(75) Inventors: Lyle Armstrong, Northumberland; Arthur James, Newcastle Upon Tyne, both of (GB); Daniel Monget, St Sorlin en Bugey; Sylvain Orenga, Neuville sur Ain, both of (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/646,967

(22) PCT Filed: Apr. 2, 1999

(86) PCT No.: PCT/FR99/00781

§ 371 Date: Nov. 15, 2000

§ 102(e) Date: Nov. 15, 2000

(87) PCT Pub. No.: WO99/51767

PCT Pub. Date: Oct. 14, 1999

(30) Foreign Application Priority Data

Apr. 2, 1998 (FR) .............................. 98 04332

(51) Int. Cl.$^7$ .............................. C12Q 1/34; C12Q 1/00; C12Q 1/37
(52) U.S. Cl. ...................... 435/18; 435/283.1; 435/975; 435/24; 435/4
(58) Field of Search ............................... 435/18, 283.1, 435/975, 24, 4

(56) References Cited

U.S. PATENT DOCUMENTS

| | | | |
|---|---|---|---|
| 4,588,836 A | 5/1986 | Matsumoto et al. | 435/15 |
| 4,603,108 A | 7/1986 | Bascomb | 435/34 |
| 4,637,979 A | 1/1987 | Skjold et al. | 435/19 |
| 4,681,841 A | 7/1987 | Matsumoto et al. | 435/18 |

FOREIGN PATENT DOCUMENTS

| | | |
|---|---|---|
| DE | 43 24 392 A1 | 1/1995 |
| EP | 0 053 470 | 6/1982 |
| EP | 0 122 028 | 10/1984 |
| EP | 0 138 530 | 4/1985 |
| EP | 0 150 227 | 8/1985 |
| FR | 2 708 286 | 2/1995 |

OTHER PUBLICATIONS

Corbett, XP–002087428 Benzoquinone Imines, Part VIII. Mechanism and Kinetics of the Reaction of p–Benzoquinone Monoimines with Monohydric Phenols.

Primary Examiner—Louise N. Leary
(74) Attorney, Agent, or Firm—Oliff & Berridge, PLC

(57) ABSTRACT

The invention concerns a chromogenous substrate for detecting the presence of at least one enzyme enzymatic activity. The invention also concerns a method for using such a substrate. The invention further concerns a method for identification based on such substrates and a device for implementing said identification method. The invention is characterized in that the substrate consists of at lease two molecules, a first molecule consisting of a non-chromogenous marker part associated with at least a specific target part for the enzyme and a second molecule consisting of a non-chromogenous part, and the non-chromogenous marker part, once it is released, reacts with the second molecule to form a chromogenous molecule. The invention is particularly applicable in bacteriology.

16 Claims, No Drawings

CHROMOGENIC SUBSTRATES FOR DETECTING BACTERIAL HYDROLASES

The present invention relates to the detection of enzymes of hydrolase type, in particular peptidases, by using effective chromogenic substrates. The present invention also relates to a process and a device for identifying microorganisms which are both simple and reliable.

Specific substrates have been used for many years to determine the presence or absence of enzymatic activities characteristic of bacteria. By the choice of substrates, depending on whether or not there is a reaction, it is possible to characterize the nature of a genus of bacteria or to differentiate between the species of a given bacterial genus.

Synthetic substrates of enzymes consist of two portions, a first portion which is specific for the enzymatic activity to be detected, and a second portion which acts as a label, and which is referred to herein-below as the labeling portion.

These specific substrates can be fluorescent or chromogenic substrates. In point of fact, it is the second portion or labeling portion which is fluorescent or chromogenic, when it is not combined with the first portion.

Fluorescent substrates may be of diverse composition.

First of all, substrates based on umbelliferone or aminocoumarin, and the derivatives thereof substituted in position 2, which allow the release of a fluorescent compound whose color ranges from blue to green under an ultraviolet (UV) lamp ($\lambda_{ex}$=365 nm).

Next, substrates based on resorufin (and derivatives), in which there is release of a compound which is fluorescent pink under natural light ($\lambda_{ex}$=530 nm).

Finally, substrates based on fluorescein (and derivatives) which, after degradation, releases a compound which is fluorescent yellow under natural light ($\lambda_{ex}$=485 nm).

These substrates are unsuitable for use in agar media, and are used more in liquid medium.

The chromogenic substrates may also be of diverse nature.

Firstly, there are substrates based on indoxyl and its derivatives which, in the presence of oxygen, produce a precipitate ranging from blue to pink.

Their applications are essentially limited to osidases and esterases and do not concern the detection of a peptidase activity. Whereas they are well suited to use on a solid support (filter, agar, electrophoresis gel, etc.), they are less well suited to the use in liquid aqueous medium (formation of a precipitate).

Secondly, there are substrates based on hydroxyquinoline or esculetin and their derivatives, which produce a brown precipitate in the presence of iron salts.

In this case also, their applications are limited to osidases and esterases. They are suitable for use on a solid support, and relatively unsuitable for use in liquid aqueous medium.

Thirdly, there are substrates based on nitrophenol and nitroaniline and derivatives, which lead to the formation of a yellow compound.

They make it possible to detect osidase and esterase activities in the case of nitrophenol-based substrates, and peptidase activities in the case of nitroaniline-based substrates. However, in the case of detecting peptidase activities, the nitroaniline released is toxic to the bacteria which it is desired to identify or characterize, which may have a negative impact on current or subsequent analyses. Moreover, they are relatively unsuitable for use on a solid support, and are better suited to use in liquid medium. Furthermore, they are not particularly chromogenic on account of the relatively low extinction coefficient of the color (yellow) which gives a relatively weak contrast in biological media.

Fourthly, there are substrates based on naphthol and naphthylamine and its derivatives. In this case, the reaction is carried out in two stages; the naphthol or naphthylamine released by the enzymatic activity undergoes an "azo-coupling" in the presence of a diazonium salt which is added at the detection stage, leading to the formation of a colored insoluble compound.

They make it possible to detect osidase and esterase activities by means of naphthol, and peptidase activities by means of naphthylamine. The azo-coupling reaction is carried out in a medium which is often chemically corrosive and toxic to bacteria, making the sample unusable for other analyses, and, what is more, naphthylamines are carcinogenic.

To detect naphthylamine and thus a peptidase activity, it is also possible to add p-dimethylamino-cinnamaldehyde in acidic medium at the end of the enzymatic reaction, instead of a diazonium salt, although this still has toxicity drawbacks with respect to the sample analyzed.

Patent application FR-A-2 708 286 proposes the use of a mixture of chromogenic substrates, each chromogen giving a particular coloration for a specific enzyme which is different from the coloration and enzyme associated with the other chromogen. When the two colorations and thus the two enzymes are present, there is formation of a "tertiary coloration".

However, this technique is unsatisfactory since, as a function of the low concentration of one of the two enzymes, it is not possible to detect this enzymatic activity which is thus masked by the coloration associated with the enzyme whose concentration is predominant.

Finally, patents U.S. Pat. No. 4,681,841 and U.S. Pat. No. 4,588,836 describe an indirect method for detecting a single enzymatic activity using a coupling between an aminobenzene and a hydroxyaromatic derivative (for example α-naphthol), this coupling leading to the formation of a chromogenic indicator in the presence of oxidase. One of the two compounds (the aminobenzene) forms part of the composition of the starting substrate; if the desired enzymatic activity is present, this compound will be released and will be able to react with the other compound.

Nevertheless, in order for the detection of the desired enzyme to be possible, the presence of oxidase in the reaction medium is an absolute necessity. However, although this information discourages a person skilled in the art from looking for a solution which does not use oxidase, the Applicant has proved, by numerous tests carried out in its laboratories, that it is possible to detect the desired enzyme by means of using, for example, aminobenzene and α-naphthol, without the addition of oxidase.

It may thus be readily appreciated that no chromogenic substrate which is particularly effective and advantageous as regards detecting at least one peptidase activity currently exists.

As regards the identification process and device, the state of the art consists of an identification process which involves a three-step manipulation:

taking a sample of the colony to be identified, carrying out an orinetation test, and looking for colonies similar to those observed and preparing an inoculum.

The orientation test should be performed before using an identification system. This is especially the case for Gram staining which requires an observation by microscope.

However, this coloration is not always easy to carry out and above all to interpret. Moreover, the cost of this test is far from negligible.

One of the aims of the present invention is thus to create a link between a culture medium and antibiotic assay and identification systems, offering biologist the possibility of performing a simple one-step test both for confirming the result of the Gram staining and for preparing the inoculum. Thus, the choice of antibiotic assay and identification tests is made reliable.

Patent application EP-A-0 122 028 proposes a colorimetric method for detecting the presence of at least one enzyme suspected of being present in a biological sample. It recommends the preparation of an absorbent brush, absorbing in this material at least one susbstrate which is specific for the enzyme which it is desired to detect. The absorbent material containing the substrate(s) is dried before use.

The invention allows the colormetric detection of enzymatic activities of hydrolase (osidase, esterase, phosphatase or peptidase) type with the aid of synthetic substrates based on two compounds, as well as a novel process which can be applied to both liquid and solid reaction media.

The invention also proposes a process and a device for identifying microorganisms, which orient the identification, and allow the recovery of said microorganisms in order to allow an inoculum to be prepared. This inoculum makes it possible to use the same microorganisms for one or more other steps, such as an identification or an antibiotic assay.

After hydrolyzing the substrates, the enzymatic activities are detected on the basis of the formation of a colored complex from the oxidative coupling of the two compounds mentioned above. This oxidative coupling can be facilitated by an oxidizing agent added to the reaction medium or produced during a metabolic process within this medium, or more simply by the presence of endogenous oxygen in this same medium.

According to a first interpretation, the present invention relates to a combination of two distinct entities, one being a nonchromogenic molecule and the other being the substrate for detecting the presence of the enzymatic activity or at least one enzyme. The substrate is characterized in that in consists of a specific portion of the enzyme, and of a nonchromogenic molecule other than the first molecule, which constitutes the labeling portion of the substrate; the two nonchromogenic molecules react together when they are in free form and can generate a chromogenic molecule.

Still according to this first interpretation, the invention also relates to a combination of two distinct entities, each corresponding to a different substrate and making it possible to detect the presence of the enzymatic activity of at least two enzymes. Each substrate is characterized in that it consists of a specific portion of the desired enzyme, and of a nonchromogenic molecule constituting the labeling portion of the substrate, and in that the two nonchromogenic molecules corresponding to the two substrates react together when they are in free form and can generate a chromogenic molecule.

According to a second interpretation, which will be used more particularly hereinbelow, to arrive at this result, it is necessary to use a new form of substrates. Thus, the substrate according to the invention comprises two different molecules. One of the molecules consists of a specific portion, an enzymatic activity and a labeling portion, which is distinct for a chromogenic molecule. The other molecule always comprises the labeling portion, distinct for a chromogenic molecule, which is free or associated with at least one specific portion, of an enzymatic activity. The object of the invention is thus, if the enzymatic activity(ies) is (are) present, to reveal the formation of a chromogenic molecule which is effective only when the two labeling portions, once released, have become associated.

To this end, the present invention relates to a chromogenic substrate for detecting the presence of the enzymatic activity of at least one enzyme, characterized in that it consists of at least two molecules, a first molecule consisting of a nonchromogenic labeling portion associated with at least one specific target portion of the enzyme and a second molecule consisting of another nonchromogenic substance, and in that the nonchromogenic labeling portion, once released, reacts with the second molecule to form a chromogenic molecule.

The present invention also relates to a chromogenic substrate for detecting the presence of the enzymatic activity of at least two enzymes, characterized in that it consists of at least two molecules, a first molecule consisting of a nonchromogenic labeling portion associated with at least one specific target portion of the first enzyme and a second molecule consisting of another nonchromogenic labeling portion associated with a specific target portion of the second enzyme, and in that the nonchromogenic labeling portions, once released, react to form a chromogenic molecule.

Irrespective of the method of preparation of the substrate, the nonchromogenic labeling portion of the first molecule consists of aminobenzene or a derivative thereof:

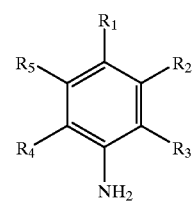

that [sic] the nonchromogenic labeling portion of the second molecule consists of α-naphthol or a derivative thereof:

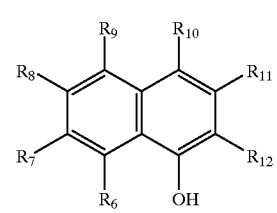

and that [sic] the chromogenic molecule obtained consists of:

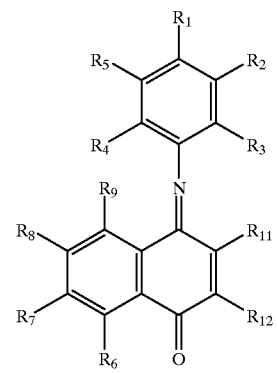

In this case, the radical $R_1$ consists of —OH, —SH or

the radical $R_{10}$ consists of —H or an atom, such as —Br, —Cl or —I, or a group of atoms, such as —SH, which can be removed during the oxidative coupling, and each radical $R_2$ to $R_9$, $R_{11}$, or $R_{12}$ consists of —H, —OH, —Br, —Cl, —I or other more complex substituents, such as —CH$_3$, —CH$_2$CH$_3$, —OCH$_3$, —OCH$_2$CH$_3$ or —COOH.

In the case of the radical $R_1$, X/or Z consists of —H, or other more complex substituents, such as —CH$_3$, —CH$_2$CH$_3$,

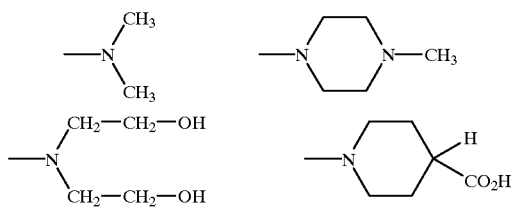

According to one embodiment, at least one of the pairs of radicals $R_2/R_3$ and $R_4/R_5$ consists of an aromatic, alicyclic or heterocyclic system.

The present invention also relates to a process for detecting an enzymatic activity via substrates, as described above, which consists in:

placing the substrates in contact with bacteria of at least one type, waiting for the bacteria to hydrolyze the substrates, and detecting the enzymatic activities based on the formation of a colored complex from the oxidative coupling of the two labeling portions.

Another object of the present invention is to propose a process, in which the molecules are present in an absorbent material and are placed in contact with the sample, and, after detection, the microorganisms thus withdrawn are resuspended in order to allow subsequent analyses (identifications, antibiotic assays, etc.).

The molecules and other compounds forming part of the reaction composition contained in the absorbent material are:

the first molecule consisting of aminobenzene or a derivative thereof, and the second molecule consisting of α-naphthol or a derivative thereof.

The reaction composition also contains an oxidizing agent, such as potassium ferricyanide.

Among the other compounds, it is also possible to have a reaction activator, such as a small amount of the first molecule and/or of the second molecule, which is (are) present in the sample to be tested.

Still among the other compounds, it is possible for the composition to comprise a binder or adhesive, such as PolyVinylPyrrolidone (PVP).

The process can be used for the Gram identification of a bacterial species to be tested and, in this case, the first molecule consists of AlaDMpPD and that [sic] the second molecule consists of α-naphthol.

Furthermore, the composition of the reaction mixture absorbed by the absorbent material is as follows:

α-naphthol from 0.01 g/l to 5 g/l, preferably from 0.1 g/l to 1 g/l, and for example 0.5 g/l, potassium ferricyanide from 0.01 g/l to 5 g/l, preferably from 0.1 g/l to 1 g/l, and for example 0.5 g/l, and AlaDMpPd from 0.01 g/l to 5 g/l, preferably from 0.1 g/l to 1 g/l, and for example 0.35 g/l.

According to one variant, the activator consists of AlaDMpPD at a concentration of from 0.01 g/l to 0.5 g/l, preferably from 0.05 g/l to 0.1 g/l, and for example 0.075 g/l.

According to another variant, the composition also comprises from 1 g/l to 50 g/l, preferably from 10 g/l to 25 g/l, and for example 15 g/l, of PVP.

The invention also relates to the use of substrates, as described above, for detecting an enzymatic activity of peptidase type.

Finally, the present invention relates to an identification device for carrying out the identification process described above, which consists of a support, for example made of plastic, which is inert with respect to the absorbent material and to the substrate(s) it contains and/or with respect to the test sample, on which is mounted a head made of an absorbent material, such as viscose.

I-Novel chromogenic substrates and implementation process:

The invention, which will be described below, relates to a few specific embodiments of the invention. These embodiments therefore do not limit the scope of the present invention which can be used for detecting enzymatic activities of any type, of hydrolase type, and for microorganisms of any genus or type.

The chromogenic substrate for detecting the presence of the enzymatic activity of at least one enzyme consists of at least two molecules, a first molecule consisting of a nonchromogenic labeling portion associated with at least one specific target portion of the enzyme and a second molecule consisting of another nonchromogenic substance. The nonchromogenic labeling portion, once released, reacts with the second molecule to form a chromogenic molecule.

In another case, the chromogenic substrate for detecting the presence of the enzymatic activity of at least two enzymes consists of at least two molecules, a first molecule consisting of a nonchromogenic labeling portion associated with at least one specific target portion of the first enzyme and a second molecule consisting of another nonchromogenic labeling portion associated with a specific target portion of the second enzyme. Once released, the nonchromogenic labeling portions react to form a chromogenic molecule.

In the case of the detection of only one enzymatic activity, there are two nonchromogenic molecules, i.e. a first molecule having a portion which is specific for the enzymatic activity to be detected and a labeling portion, whereas the second molecule consists only of the labeling portion. The two labeling portions consist respectively of compounds I and II below:

Compound I

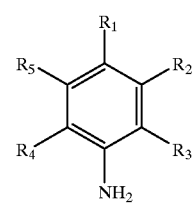

-continued

Compound II

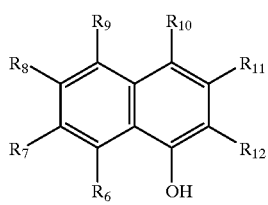

in which:

$R_1$=—OH or —SH or

with X and/or Z=—H or other more complex substituents, such as —$CH_3$, —$CH_2CH_3$,

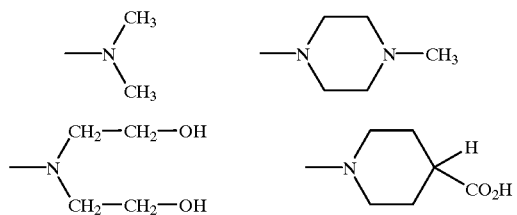

$R_{10}$=—H or a group or atom which can be removed during the oxidative coupling, such as —Br, —Cl, —I, —SH, etc., $R_2$, $R_3$, $R_4$, $R_5$, $R_7$, $R_8$, $R_9$, $R_{11}$ and $R_{12}$=—H, —OH, —Br, —Cl, —I, —$CH_3$, —$CH_2CH_3$, —$OCH_3$, —$OCH_2CH_3$, —COOH, or any other more complex substituent, $R_2/R_3$ and $R_4/R_5$ also possibly forming part of an aromatic, alicyclic or even heterocyclic system, such as:

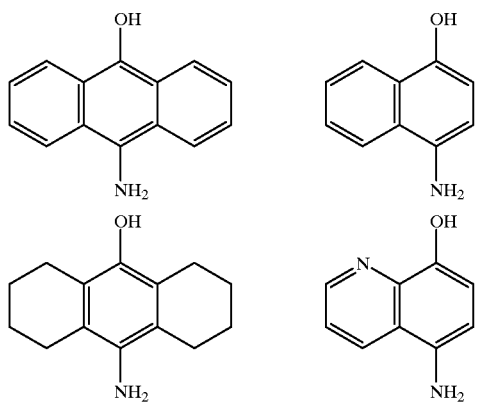

Compound III obtained by combining the two compounds I and II is thus as follows:

Compound III

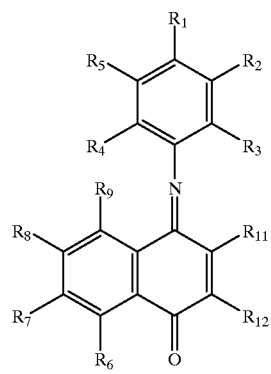

To understand the invention, it is recalled that the formula of a hydrolase enzyme substrate may be represented schematically in the form:

A—O—B, if it is an osidase, phosphatase, esterase or sulfatase substrate.

The enzymatic hydrolysis may then be written as:

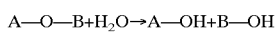

with, according to the invention:

A—OH=ose, phosphate, sulfate, fatty acid (from the simplest, i.e. acetic acid), and B—OH=compound I with $R_1$=—OH or compound II.

A—CO—NH—B, if it is a peptidase substrate.

The enzymatic hydrolysis can then be written as:

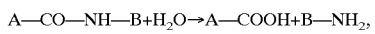

with, according to the invention:

A—COOH=amino acid or chain of amino acids possibly ending with a blocking agent, and B—$NH_2$=compound I.

The process according to the invention uses, on the one hand, an enzymatic substrate as described above, based on:

either a compound I derived from aminobenzene, with $R_1$=—OH for the osidase, phosphatase or esterase substrates, or a compound II derived from α-naphthol (with the exclusion of peptidase substrates), on the other hand, a revealing agent which is initially present in the reaction medium or which can be added during or after the enzymatic reaction, this agent being:

either compound II for the detection of compound I resulting from the enzymatic hydrolysis of the substrates based on the latter compound, and or compound I for the detection of compound II resulting from the enzymatic hydrolysis of the substrates based on the latter compound.

The formation in the reaction medium of the colored compound III (derived from indophenol) from the oxidative coupling of I and II makes it possible to detect the hydrolysis of the substrate and thus the enzymatic activity involved.

The color of compound III depends on the substituents on compounds I and II.

For example, it is purple if $R_1$=—OH and $R_2$ to $R_{11}$=—H, or blue if $R_1$=—OH, $R_2$ and $R_5$=—Cl and $R_3$ to $R_{11}$=—H.

The process thus described is, in particular, extremely advantageous for calorimetrically detecting activities of peptidase type. Specifically, according to the prior art, the choice of colored reactions was limited to the use of substrates based on nitroaniline, which is relatively nonchromogenic, and of substrates based on naphthylamine, which is highly toxic, necessitating the addition of a reagent at the end of the reaction (for example a diazonium salt) to detect the amine released.

The invention proposes a novel type of substrates for peptidases, based on aminobenzene or derivatives (compound I).

Gradually as this compound I is released into the reaction medium during the enzymatic hydrolysis, it forms a strongly colored complex (generally colored red to blue) by oxidative coupling with α-naphthol or a derivative (compound II) present in this medium.

The coupling reaction can also be obtained at the end of the test if the addition of compound II is carried out at the end of the enzymatic reaction.

Another important advantage of the invention consists in combining two substrates in the reaction medium, according to the process, one based on compound I and the other based on compound II.

Any type of combination of simultaneous detection of two enzymatic activities (for example a peptidase and an osidase, an esterase and an osidase, two osidases, etc.) may thus be envisaged. In these cases, the colored complex III will be formed only if the two substrates are hydrolyzed. This combination may be very useful for diagnostic tests which require high specificity, in particular when it is a case of characterizing microorganisms.

One of the examples mentioned illustrates the advantage of this simultaneous detection of two enzymatic activities in the field of identifying bacteria.

Among the other advantages of the invention, it is possible to give compound I a double functionality. Specifically, it is possible to chemically graft onto compound I, on the one hand onto the —$NH_2$ group, an amino acid or a chain of amino acids possibly ending with a blocking agent, and, on the other hand, onto $R_1$, if it is a hydroxyl (—OH) group, an ose, a phosphate or a fatty acid. A molecule is obtained which may be termed a double substrate and which, in order to generate compound I in free form in the reaction medium, should be hydrolyzed by two distinct enzymatic activities, on the one hand a peptidase, and on the other hand an osidase, phosphatase or esterase, depending on the nature of the product grafted onto $R_1$.

Thus, in the presence of compound II, the colored complex III can only be obtained if the two enzymatic activities are present. The advantage of such substrates with double functionality lies in their very high specificity which may be exploited to characterize microorganisms, for example.

In the same sense, a mixture of a substrate with double functionality based on compound I, as described above, and a substrate based on compound II may be envisaged according to the invention to search for another osidase, phosphatase or esterase. In this case, the production of the colored complex III requires the simultaneous presence of three enzymatic activities, in order to release compounds I and II. Two enzymatic activities make it possible to hydrolyze the molecule based on compound I and one enzymatic activity makes it possible to hydrolyze the molecule based on compound II. The specificity of the test is thus further increased.

According to the invention, it is also possible to combine different types of substrates in the same reaction medium, in particular substrates known in the prior art and substrates according to the process claimed. This makes it possible to carry out different colored reactions, and thus to simultaneously detect several enzymatic activities in the same reaction medium.

The invention can be applied to the search for enzymatic activities in different types of biological or nonbiological samples.

The invention can also be used to characterize microorganisms such as bacteria or yeasts. In this case, the enzymatic tests can be performed in liquid medium in individual tubes or in compartmentalized supports, such as microtitration plates, for example. They can also be performed in agar medium (for example in Petri dishes) with staining of the colonies producing the desired enzymatic activities.

The present invention thus relates to a process for detecting an enzymatic activity by means of substrates, as described above, which consists in:

placing the substrates in contact with bacteria of at least one type, waiting for the bacteria to hydrolyze the substrates, and detecting the enzymatic activities based on the formation of a colored complex from the oxidative coupling of the two labeling portions.

The oxidative coupling is facilitated either by:

the addition of at least one oxidizing agent to the reaction medium, the production, during a metabolic process in this reaction medium, of at least one oxidizing agent, the presence of endogenous oxygen in said reaction medium.

The examples given below will allow the invention to be understood more clearly. They relate specifically to the field of bacteriology, but it is clear that the process can be applied to any other field of enzymology which involves looking for hydrolases.

EXAMPLE 1

Detection of β-glucosidase in Liquid Medium (method 1)

The reaction medium proposed in this example has the formulation:

| | |
|---|---|
| meat peptone | 10 g |
| NaCl | 5 g |
| α-naphthyl-β-glucopyranoside | 0.5 g |
| 4-aminophenol | 50 mg |
| $H_2O$ | 1000 ml |
| pH | 7.0 |

This medium is sterilized by filtration through a 0.22μ Millipore filter and distributed into sterile tubes at a rate of 5 ml per tube.

The test to search for β-glucosidase is performed on 4 strains cultured for 24 h at 35–37° C. on Trypticase-Soya agar. These strains belong, respectively, to the species:

*Escherichia coli,*

*Staphylococcus sciuri,*

*Streptococcus pyogenes,*

*Enterococcus faecalis.*

Starting with the above cultures, aqueous suspensions adjusted to 0.5 McFarland are prepared.

100 microliters of these suspensions are used to inoculate four tubes of reaction medium, each tube corresponding to a strain.

The stoppered tubes are incubated at 35–37° C. for 18 to 24 h.

After incubation, the appearance of a purple coloration is observed, corresponding to the formation of the indophenol complex and reflecting the presence of a β-glucosidase activity.

The results obtained are as follows:

| Strain | Expected theoretical result | Result obtained |
|---|---|---|
| E. coli | − | − |
| S. sciuri | + | + |
| S. pyogenes | − | − |
| E. faecalis | + | + |

EXAMPLE 2

Detection of β-glucosidase in Liquid Medium (method 2)

The reaction medium proposed in this example has the formulation:

| | |
|---|---|
| meat peptone | 10 g |
| NaCl | 5 g |
| α-naphthol | 50 mg |
| 4-aminophenol-β-D-glucopyranoside | 0.5 g |
| H₂O | 1000 ml |
| pH | 7.0 |

The preparation of the medium, the choice of test strains and the implementation of the test are identical to the procedure described in Example 1.

The appearance of a purple coloration due to the formation of the indophenol complex indicates the presence of a β-glucosidase activity.

The results obtained are identical to those of Example 1, i.e.:

| Strain | Expected theoretical result | Result obtained |
|---|---|---|
| E. coli | − | − |
| S. sciuri | + | + |
| S. pyogenes | − | − |
| E. faecalis | + | + |

These results show that it is possible to detect an activity of osidase type using according to the invention either a substrate based on compound I or a substrate based on compound II. This would likewise be the case for the investigation of activities of esterase or phosphatase type.

EXAMPLE 3

Detection of Pyroglutamyl-amino-peptidase in Liquid Medium:

The reaction medium proposed in this example has the formulation:

| | |
|---|---|
| meat peptone | 10 g |
| NaCl | 5 g |
| α-naphthol | 50 mg |
| L-pyroglutamyl-4-amino-2,6-dichlorophenol | 0.5 g |
| H₂O | 1000 ml |
| pH | 7.0 |

The preparation of the medium, the choice of test strains and the implementation of the test are identical to the procedure described in Example 1.

The appearance of a blue coloration due to the formation of the indophenol complex reveals a pyroglutamyl-aminopeptidase activity. It should be noted that the blue color results from the presence of chlorine groups in positions 2 and 6 on the 4-aminophenol.

The results obtained are as follows:

| Strain | Expected theoretical result | Result obtained |
|---|---|---|
| E. coli | − | − |
| S. sciuri | − | − |
| S. pyogenes | + | + |
| E. faecalis | + | + |

EXAMPLE 4

Combined Investigation of Two Enzymatic Activities According to the Process of the Invention Application to the Simultaneous Detection of β-glucosidase and Pyroglutamyl-aminopeptidase The reaction medium proposed in this example has the formulation:

| | |
|---|---|
| meat peptone | 10 g |
| NaCl | 5 g |
| α-naphthyl-b-D-glucopyranoside | 0.5 g |
| L-pyroglutamyl-4-amino-2,6-dichlorophenol | 0.5 g |
| H₂O | 1000 ml |
| pH | 7.0 |

The preparation of the medium, the choice of test strains and the implementation of the test are identical to the procedure described in Example 1.

The appearance of a blue coloration due to the formation of the indophenol complex is possible only if the two substrates are hydrolyzed. This therefore reflects a combination of β-glucosidase and pyroglutamyl-aminopeptidase activities in the same reaction medium. The absence of one of the activities prevents the formation of the colored complex.

The results obtained are as follows:

| Strain | Expected theoretical result | Result obtained |
|---|---|---|
| E. coli | − | − |
| S. sciuri | − | − |
| S. pyogenes | − | − |
| E. faecalis | + | + |

This example clearly illustrates one of the advantages of the invention by allowing greater selectivity in the characterization of the microorganisms (E. faecalis in this application).

EXAMPLE 5

Characterization of Bacteria in Agar Medium by Simultaneous Investigation of β-galactosidase (βGAL) and L-alanine-aminopeptidase (Ala) Activities α-Naphthyl-β-D-galactopyranoside and L-alanyl-N,N'-dimethyl-p-phenylenediaminenaphthalenesulfonyl-ydrazide are added to a trypticase soya agar medium. This substrate is derived from compound I according to the invention.

The medium is distributed and inoculated in the following way:
six dishes with pure cultures:
   Escherichia coli [βGAL (+), Ala (+)]
   Klebsiella pneumoniae [βGAL (+), Ala (+)]
   Salmonella typhimurium [βGAL (−), Ala (+)]
   Pseudomonas aeruginosa [βGAL (−), Ala (+)]
   Staphylococcus xylosus [βGAL (+), Ala (−)]
   Candida albicans [βGAL (−), Ala (−)].
two dishes with the mixtures of strains E. colii/S. xylosus and S. typhimurium/C. albicans.

The media are incubated at 35–37° C. After incubation of 18–24 h, only the dishes containing the E. coli and K. pneumoniae strains [⊖GAL (+), Ala (+)] contain blue-stained colonies.

With the mixture E. coli/S. xylosus, only the E. coli colonies are blue, those of S. xylosus remaining colorless.

Just as in Example 4, the production of the colored complex III based on indophenol thus necessitated the joint presence of two enzymatic activities, in this case β-galactosidase and L-alanine-aminopeptidase.

However, the presence of only one or of neither of these two activities does not result in formation of the colored complex.

As is the case in Example 5, the choice of a suitable phenylenediamine derivative makes it possible to obtain a coloration which remains in the immediate vicinity of the colonies and thus to distinguish two different populations in a mixture.

This example shows that it is possible, according to the invention, to specifically colored [sic] colonies at the surface of an agar medium and thus to characterize them. In the present case, it may be applied to the detection of coliform bacteria which are Gram-negative bacilli having both β-galactosidase and L-alanine-aminopeptidase activity.

EXAMPLE 6

Combined Investigation of Three Enzymatic Activities According to the Process of the Invention Application to the Simultaneous Detection of β-galactosidase (βGAL), β-glucosidase (βGLU) and L-alanine-aminopeptidase (Ala)

The reaction medium proposed in this example has the formulation:

| | |
|---|---|
| meat peptone | 10 g |
| NaCl | 5 g |
| α-naphthyl-b-D-glucopyranoside | 0.5 g |
| L-alanyl-4-amino-2,6-dichlorophenyl-β-D-galactopyranoside | 0.5 g |
| $H_2O$ | 1000 ml |
| pH | 7.0 |

The preparation of the medium is identical to the procedure described in Example 1.

The test for investigation of the 3 enzymatic activities is performed on 5 strains cultured for 24 h at 35–37° C. on Trypticase-Soya agar. These strains belong respectively to the species:

Escherichia coli [βGAL (+), βGLU (−), Ala (+)]
Klebsiella pneumoniae [βGAL (+), βGLU (+), Ala (+)]
Salmonella typhimurium [βGAL (−), βGLU(−), Ala (+)]
Stenotrophomonas maltophilia [βGAL (−), βGLU (+), Ala (+)]
Staphylococcus saprophyticus [βGAL (+), βGLU (−), Ala (+)]

The appearance of a blue coloration due to the formation of the indophenol complex is possible only if the three substrates are hydrolyzed. It thus reflects a combination of β-galactosidase, β-glucosidase and L-alanine-aminopeptidase activities in the same reaction medium, as is the case for the strain of K. pneumoniae. The absence of one of the activities prevents formation of the colored complex.

The results obtained are as follows:

| Strain | Expected theoretical result | Result obtained |
|---|---|---|
| E. coli | − | − |
| K. pneumoniae | + | + |
| S. typhimurium | − | − |
| S. maltophilia | − | − |
| S. sapropriticus | − | − |

This example once again shows the potentials of the invention for carrying out highly selective tests.

The six examples given only describe enzymatic tests according to the invention.

It is quite clearly possible to combine these tests with the known tests of the prior art, using chromogenic or fluorogenic substrates.

II-Identification process and device:

The principle of the medium, used with the identification process and device, is based on the use of the twinned substrates described above.

According to a representative example, the GRAM identification process uses a substrate based on aminobenzene or a derivative thereof, such as DiMethyl-paraPhenyleneDiamine (DMpPD). In the example which follows, the substrate consists of Alanine-Dimethyl-paraPhenyleneDiamine (AlaDMpPD). The activity demonstrated is thus the Alanine-aminopeptidase, this activity being specific for Gram-negative bacteria.

It functions as follows. Enzymatic hydrolysis causes release of the DMpPD group. Next, the DMPD binds with α-naphthol (or a derivative) by oxidative coupling facilitated by an oxidizing agent, potassium ferricyanide ($K_3Fe(CN)_6$). This then causes formation of a violet-gray complex.

In a first stage, the device is defined in the following way:
a biogelytone medium containing as substrate: AlaDMpPD, and
a bottle brush impregnated with a reaction mixture consisting of α-naphthol and potassium ferricyanide.

Another device has been defined, which is even more specific in Gram identification and which can also be used with blood agars of Columbia type. It consists of:
a medium consisting of a blood agar of Columbia type (with or without AlaDMpPD), and
a reaction mixture which impregnates a bottle brush and which is constituted on the basis of α-naphthol, potassium ferricyanide and AlaDMpPD and then dried.

This reaction mixture contained in the bottle brush was further improved by adding a step of drying the bottle brushes, which facilitates their subsequent manipulation.

The exact composition is as follows:
for the agar, presence or absence of AlaDMpPD at 0.075 gram per liter (g/l), and
for the bottle brush:
α-naphthol from 0.01 to 5 g/l, preferably from 0.1 to 1 g/l, and for example 0.5 g/l,
potassium ferricyanide from 0.01 to 5 g/l, preferably from 0.1 to 1 g/l, and for example 0.5 g/l, and
AlaDMpPD from 0.01 to 5 g/l, preferably from 0.1 to 1 g/l, and for example 0.35 g/l.

The results obtained in terms of sensitivity and specificity are thus the best obtained. In this case, the detection of the reaction is not instantaneous. It takes 15 to 30 seconds (s) to observe the appearance of any coloration, this being the time required for hydrolysis of the substrate by the bacterial aminopeptidase.

Sixty-one strains on different media such as: Polyvitex chocolate agar (registered trademark), CPS ID2 medium (registered trademark), TSA +/− blood and Columbia +/− blood were tested with bottle brushes impregnated with α-naphthol, potassium ferricyanide and AlaDMpPD and then dried. This study showed that this system was compatible with the majority of conventional media and common chromogenic agents.

To further improve the reaction time, a reaction activator is incorporated into the medium.

In this context of activating the reaction, it was found that the addition to the medium of a small amount of AlaDMpPD and/or of α-naphthol allows the reaction to be detected without reducing the sensitivity. Furthermore, the detection time is thus considerably reduced, since it is taken from 0 to 10 s [sic]. This small amount corresponds to a concentration of from 0.01 to 0.5 g/l, preferably from 0.05 to 0.1 g/l, and for example 0.075 g/l.

According to one embodiment, it is also possible to add a binder to the bottle brush. The addition of a binder makes it possible both to gather together the fibers in the head of the bottle brush and to limit the release of products present on the bottle brush into the inoculum suspension. Such a binder can consist of PolyVinylPyrrolidone (PVP), which in fact makes it possible not only to satisfy the above criteria but also to substantially increase the specificity. In the composition described above with the concentrations, the PVP is introduced into the constituents of the viscose head of the bottle brush in a concentration of from 1 to 50 g/l, preferably from 10 to 25 g/l, and for example 15 g/l.

1. Experiment

An evaluation of this medium was thus carried out on one hundred and thirty-three (133) strains divided among the following species. Table 1 below lists the species tested and the number of strains for each species.

TABLE 1

Species tested and number of strains for each species

| Species | Number of strains |
|---|---|
| *Acinetobacter baumanii* | 2 |
| *Acinetobacter junii* | 2 |
| *Citrobacter freundii* | 3 |
| *Citrobacter spp* | 1 |
| *Enterobacter cloacae* | 3 |
| *Enterobacter intermidis* | 1 |
| *Enterobacter spp* | 1 |
| *Escherichia coli* | 4 |
| *Klebsiella oxytoca* | 5 |
| *Klebsiella pneumoniae* | 4 |
| *Morganella morganii* | 4 |
| *Proteus mirabilis* | 5 |
| *Proteus vulgaris* | 5 |
| *Providencia stuartii* | 4 |
| *Pseudomonas fluorescens* | 5 |
| *Serratia marcescens* | 4 |
| *Bacillus cereus* | 4 |
| *Bacillus lentus* | 1 |
| *Bacillus mycoides* | 2 |
| *Bacillus subtilis* | 2 |
| *Corynebacterium aquaticum* | 2 |
| *Corynebacterium ulcerans* | 2 |
| *Enterococcus faecalis* | 5 |
| *Enterococcus faecium* | 3 |
| *Enterococcus gallinarum* | 3 |
| *Haemophilus haemolyticus* | 2 |
| *Haemophilus influenzae* | 2 |
| *Lactobacillus casei* | 4 |
| *Listeria monocytogenes* | 4 |
| *Staphylococcus aureus* | 3 |
| *Staphylococcus epiderinidis* | 3 |
| *Staphylococcus haemolyticus* | 3 |
| *Staphylococcus saprophyticus* | 3 |
| *Streptococcus agalactiae* | 4 |
| *Streptococcus pneumoniae* | 3 |
| *Streptococcus pyogenes* | 3 |
| *Candida albicans* | 3 |
| *Candida glabrata* | 3 |
| *Candida guilliermondii* | 1 |
| *Candida kefyr* | 1 |
| *Candida krusei* | 3 |
| *Candida parapsilosis* | 1 |
| *Candida tropicalis* | 4 |
| *Trichosporon asteroides* | 1 |
| *Trichosporon mucoides* | 1 |
| TOTAL | 133 |

Table 2 lists the results obtained:

TABLE 2

Sensitivity and specificity of the species tested

| | |
|---|---|
| Sensitivity | 93% |
| Specificity towards Gram + bacteria | 81 to 90% |
| Specificity towards yeasts | 89 to 100% |

Among the results obtained on the strains tested, certain strains are false negatives. These false negatives are two (2) of the four (4) strains of *P. aeruginosa*, two (2) of the five (5) strains of *P. fluorescens* and one (1) of the two (2) strains of *H. influenzae*. Certain strains are false positives. These false positives consist of the two (2) strains of *C. ulcerans*, one (1) of the five (5) strains of *E. faecalis*, the three (3) strains of *S. pyogenes*, two (2) of the four (4) strains of *S. agalactiae*, the strain of *C. guilliermondii* and the strain of *C. parapsilosis*.

2. Readability of the test

Virtually all of the Gram-negative bacteria, except for the Pseudomonas bacteria, give a sharp violet-gray coloration whose intensity is strictly greater than 2 (on a semiquantitative scale up to 4), while the Gram-positive bacteria or those which are false-positives, except for *S. pyogenes*, have a coloration intensity of less than 1 on this same scale.

3. Detection time

About 90% of the Gram-negative bacteria are detected between 0 and 10 s; most of the Gram-positive bacteria or those which are false-positives are detected after 10 s, apart from the strains of *S. pyogenes*.

The current medium thus has good sensitivity and good specificity. The other false-positive strains are generally of very weak intensity and have a detection time of greater than 10 s. These strains are thus rather [sic] dubious strains rather than false-positives.

4. Definition of the bottle brush

The bottle brush model, which is particularly advantageous, is a bottle brush which satisfies the following criteria:

a plastic stick 2.5 millimeters (mm) in diameter and 150 mm in length, and with a viscose head less than or equal to 4.5 mm in diameter.

5. Method for manufacturing and manipulating the bottle brushes

The manufacturing conditions are as follows:

soaking in a solution as defined above for 2 to 3 minutes (min), drying for 2 hours (h) at 37° C., and packaging in a leakproof plastic bag protected from the light.

6. Packaging of the bottle brushes

The bottle brushes can be stored, for example, in a sterile manner (gamma rays) in wrapping containing one (1), twenty five (25) or one hundred (100) to one thousand (1000) of these bottle brushes. However, a packaging of from twenty (20) to twenty five (25) bottle brushes not necessarily sterilized after drying is entirely conceivable. The packaging is carried out with or without a desiccant, and sheltered from the light.

7. Critical parameters

The use of the twinned substrates is thus identical to that outlined at the start of the description. Thus, the head of the bottle brush contains at least two molecules. Thus, in the example given, a first molecule (AlaDMpPD) consists of a nonchromogenic labeling portion (DMpPD) associated with at least one specific target portion (alanine) of the enzyme (Alanine-aminopeptidase) and a second molecule consisting of another nonchromogenic substance (α-naphthol), the nonchromogenic labeling portion (AlaDMpPD), once released, reacts with the second molecule (α-naphthol) to form a chromogenic molecule.

The use of the bottle brush serves as a support for reagents and allows the preparation of the inoculum suspension, which will be used in other identification and antibiotic assay systems, on the basis of the same strains which were evaluated above. This thus considerably reduces the errors during inoculation of new "similar" microorganisms for carrying out the following identification and antibiotic assay operations, etc.

Furthermore, it is also possible to prepare bottle brushes for other types of tests, for example oxidase, indole, esterase, phosphatase, etc.

What is claimed is:

1. A chromogenic substrate for detecting the presence of enzymatic activity of at least two enzymes, characterized in that said substrate consists of at least two molecules, a first molecule consisting of a nonchromogenic labeling portion associated with at least one specific target portion of the first enzyme and a second molecule consisting of another nonchromogenic labeling portion associated with a specific target portion of the second enzyme, and in that the nonchromogenic labeling portions, once released, react to form a chromogenic molecule.

2. The substrate, according to claim 1, characterized in that the nonchromogenic labeling portion of the first molecule consists of aminobenzene or a derivative thereof:

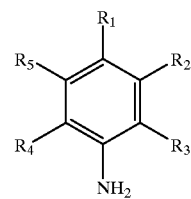

in that the nonchromogenic labeling portion of the second molecule consists of α-naphthol or a derivative thereof:

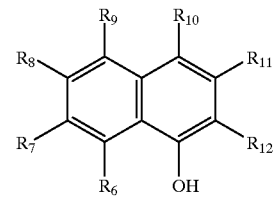

and in that the chromogenic molecule obtained consists of:

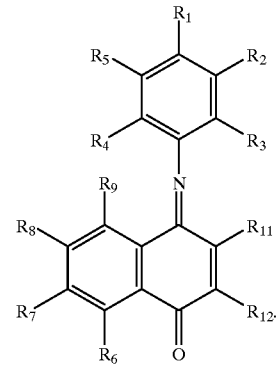

3. The substrate, according to claim 2, characterized in that the radical $R_1$ consists of —OH, —SH or

in that the radical $R_{10}$ consists of —H or an atom, such as —Br, —Cl or —I, or a group oE atoms, such as —SH, which can be removed during the oxidative coupling, and in that each radical $R_2$ to $R_9$, $R_{11}$, or $R_{12}$ consists of —H, —OH, —Br, —Cl —I or other more complex substituents, such as —CH$_3$, —CH$_2$CH$_3$, —OCH$_3$, —OCH$_2$CH$_3$ or —COOH.

4. The substrate in the case in which the radical R₁ consists of

according to claim 2, characterized in that X and/or Z consists of —H, or other more complex substituents, —CH₃, —CH₂CH₃,

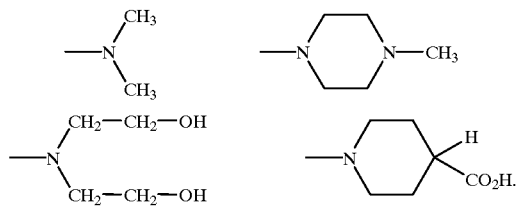

5. The substrate, according to claim 2, characterized in that at least one of the pairs of radicals R₂/R₃ and R₄/R₅ consists of an aromatic, alicyclic or heterocyclic system.

6. Process for detecting at least two enzymatic activities via substrates, charcterized in that said process consists in:

placing molecules consisting of at least two substrates in the presence of at least one type of bacteria microorganisms which is contained in a test sample, waiting for the bacteria to Hydrolyze the substrates, and detecting the enzymatic activities based on the formation of a colore complex from the oxidative coupling of the two labeling portions.

7. Process, according to claim 6, characterized in that the molecules are present in an absorbent material and are placed in contact with the sample, and after detection, the microorganisms withdrawn are resuspended in order to allow subsequent analyses, identifications, or antibiotic assays.

8. Process according to claim 6, characterized in that the molecules and other compounds forming part of the reaction composition, optionally contained in the absorbent material, are:

the first molecule consisting of aminobenzene or a derivative thereof, and/or the second molecule consisting of α-naphthol or a derivative thereof, optionally combined with a potassium ferricyanide oxidixing agent.

9. Process, according to claim 8, characterized in that it comprises a reaction activator, a small amount of the first molecule and/or of the second molecule, which is present in the sample to be tested.

10. Process, according to claim 8, characterized in that the composition comprises a PolyVinylPyrrolidone (PVP) binder.

11. Process, according to claim 8 for the Gram identification of a bacterial species to be tested, characterized in that the first molecule consists of AlaDMpPD, and in that the second molecule consists of α-naphthol.

12. Process, according to claim 8, characterized in that the composition of the absorbent material is as follows:

α-naphthol from 0.01 g/l to 5 g/l, potassium ferricyanid from 0.01 g/l to 5 g/l, and AlaDMpPd from 0.01 g/l to 5 g/l, from.

13. Process, according to claim 9, characterized in that the activator consists of Ala-DMpPD at a concentration of from 0.001 g/l to 0.5 g/l.

14. Process, according to claim 10, characterized in that the composition also comprises from 1 g/l to 50 g/l of PVP.

15. A substrate, according to claim 1, for detecting an enzymatic activity of peptidase.

16. A device for detecting, in a sample, at least two enzymatic activities, characterized in that said device comprises a support in which an absorbent viscose material is placed at least one substrate according to claim 1, and the sample, wherein said support made of plastic, being inert with respect to the absorbent material, to the substrate(s) and to the sample.

* * * * *